(12) United States Patent
Qian (10) Patent No.: US 7,217,521 B2
(45) Date of Patent: May 15, 2007

(54) SPLICING FACTOR TARGET IDENTIFICATION

(75) Inventor: Zuwei Qian, Fremont, CA (US)

(73) Assignee: Affymetrix, Inc., Santa Clara, CA (US)

( * ) Notice: Subject to any disclaimer, the term of this patent is extended or adjusted under 35 U.S.C. 154(b) by 343 days.

(21) Appl. No.: 11/016,672

(22) Filed: Dec. 17, 2004

(65) Prior Publication Data

US 2005/0227260 A1 Oct. 13, 2005

Related U.S. Application Data

(60) Provisional application No. 60/530,522, filed on Dec. 17, 2003.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3

(58) Field of Classification Search .............. 435/6; 536/23.1, 24.3
See application file for complete search history.

(56) References Cited

U.S. PATENT DOCUMENTS

| | | | | |
|---|---|---|---|---|
| 5,914,267 A | * | 6/1999 | Mertz et al. ............. | 435/320.1 |
| 6,287,768 B1 | * | 9/2001 | Chenchik et al. ............ | 435/6 |
| 6,309,822 B1 | * | 10/2001 | Fodor et al. .................. | 435/6 |
| 7,109,390 B2 | * | 9/2006 | Lyznik et al. ............... | 800/278 |
| 2004/0009512 A1 | * | 1/2004 | Ares et al. .................... | 435/6 |
| 2004/0014107 A1 | * | 1/2004 | Garcia-Blanco et al. ....... | 435/6 |

OTHER PUBLICATIONS

Adams et al., ZNF265—a novel spliceosomal protein able to induce alternative splicing. The Journal of Cell Biology 154(1) : 25-32 (Jul. 2001).*
Gerke et al., A protein associated with small nuclear ribonucleoprotein particles recognizes the 3' splice site of premessenger RNA. Cell 47 (6) : 973-984 (1986).*
Johnson et al., Genome-Wide survey of Human alternative Pre-mRNA splicing with exon junction microarrays. Science 302 : 2141-2144 (Dec. 2003).*
Kafasla et al., Association of the 72/74-kDa proteins, members of the heterogeneous nuclear ribonucleoprotein M group, with the pre-mRNA at early stages of spliceosome assembly. Biochemical Journal 363 (Pt 3) : 793-799 (2002).*
Kamma et al. Molecular characterization of the hnRNP A2/B1 proteins: Tissue-specific expression and novel isoforms. Experimental Cell Research 246 (2) : 399-411(1999).*
Kikuchi et al., Expression profiles of non-small cell lung cancers on cDNA microarrays: Identification of genes for prediction of lymph-node metastasis and sensitivity to anti-cancer drugs. Oncogene 22 : 2192-2205 (2003).*
Le Hir et al., Pre-mRNA splicing alters mRNP composition: evidence for stable association of proteins at exon-exon junctions. Genes & Development 14(9) : 1098-1108 (May 2000).*

(Continued)

*Primary Examiner*—Ethan Whisenant
(74) *Attorney, Agent, or Firm*—Sandra E. Wells (57) ABSTRACT

Methods for identifying transcripts and genes whose splicing is regulated by a selected splicing factor are disclosed. Unprocessed or partially processed transcripts are bound to an array of probes and contacted with one or more splicing factors. The identities of transcripts bound to splicing factors are determined.

20 Claims, 1 Drawing Sheet

OTHER PUBLICATIONS

Lopato et al., Pre-mRNA splicing in plants :Characterization of Ser/Arg splicing factors. PNAS 93 : 3074-3079 (1996).*

Niranjanakumari et al., Reversible cross-linking combined with immunoprecipitation to study RNA-protein interactions in vivo. Methods 26 : 182-190 (2002).*

Schaal et al., Selection and characterization of pre-mRNA splicing enhancers : Identification of novel SR protein-specific enhancer sequences. Molecular and Cellular Biology 19(3) : 1705-1719 (1999).*

Tenenbaum et al. Identifying mRNA subsets in messenger ribonucleoprotein complexes by using cDNA arrays. PNAS 97(26) : 14085-14090 (Dec. 2000).*

Zahler et al., SR Proteins: A Conserved Family of Pre-mRNA Splicing Factors. Genes & Develpoment 6 : 837-847 (1992).*

* cited by examiner

Fig. 1

SPLICING FACTOR TARGET IDENTIFICATION

RELATED APPLICATIONS

This application claims the benefit of U.S. Provisional Application No. 60/530,522 filed Dec. 17, 2003. The entire disclosure of the above application is incorporated herein by reference in its entirety for all purposes.

FIELD OF THE INVENTION

The present invention relates generally to identification of genes, transcripts or groups of transcripts that are regulated by selected splicing factors. Interaction between the selected splicing factors and the transcripts is detected by capturing the complexes on an array of probes and detecting the presence of bound complexes.

BACKGROUND OF THE INVENTION

Many spatially or temporally regulated splicing events are regulated by the binding of auxiliary RNA binding proteins. These proteins act to modulate the functionality of the constitutive splicing machinery and often target specific RNA by binding to specific sequence elements in specific RNAs or groups of RNAs. RNA binding proteins may target multiple gene products, leading to the coordinated post-transcriptional regulation of groups of genes.

SUMMARY OF THE INVENTION

In one embodiment a method of identifying a binding target for a splicing factor is disclosed. A nucleic acid sample comprising unprocessed or partially processed RNA is obtained and unprocessed or partially processed RNAs are captured on the array by hybridization to probes that are complementary to unprocessed or partially processed RNAs. The captured RNAs are mixed with a splicing factor to form complexes between the splicing factor and unprocessed or partially processed RNAs and the RNAs that form complexes with the splicing factor are identified. These RNAs are identified as targets of the splicing factor. The nucleic acid sample may be obtained by isolating nucleic acid that is bound to heterogenous nuclear ribonucleoprotein particles which may be isolated by immunoprecipitation. In a preferred embodiment the splicing factor is labeled with a detectable label, such as a fluorescent dye. The array comprises probes of known sequence at known location on the array so when splicing factor is detected in a complex in a known location the identity of the sequence of the probe in that location is also known and the identity of the bound RNA may be determined. In one embodiment an antibody is used to detect splicing factor bound to the array. The antibody may be directed to the splicing factor or the splicing factor may be tagged with an epitope and an antibody to that epitope may be used to detect bound splicing factor.

In some aspects the array comprises a plurality of probes that are complementary to regions of a genome that are predicted to be removed by post transcriptional processing events, for example, introns. Probes of the array may also include exon-intron junction probes and exon-exon junction probes.

In some aspects, the splicing factor is a complex of proteins or proteins and RNA. In some aspects more than one splicing factor may be analyzed in a single experiment.

If different splicing factors are being hybridized simultaneously to the same array each splicing factor may be labeled with a differentially detectable label. Any protein may be investigated for binding to pre-mRNA, including known or predicted splicing factors. Splicing factors may include, for example, CUG-BP, SR proteins, hnRNP proteins, CELF family proteins, DEAD box proteins, PTB, KSRP, FBP, U2AF, ASF/SF2, CUS1, CUS2, PRP proteins and Nova-1. Splicing factors that are analyzed may be from a non-cognate organisms, for example, a human nucleic acid sample may be captured and analyzed to determine which RNAs are bound by a mouse splicing factor.

Splicing factors may be labeled by incorporation of a label into the protein or by attaching a label to the protein. The protein may also be a fusion protein fused to a tag, for example, GST, or 6-Histidines. Splicing factor-pre-mRNA complexes may also be detected by an antibody that binds specifically to the protein or to a tag on the protein.

In a preferred embodiment a plurality of different transcripts that are bound by the same splicing factor or factors are identified.

DETAILED DESCRIPTION OF THE PREFERRED EMBODIMENTS a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I–IV), *Using Antibodies: A Laboratory Manual, Cells: A Laboratory Manual, PCR Primer: A Laboratory Manual*, and Molecular *Cloning: A Laboratory Manual* (all from Cold Spring Harbor Laboratory Press), Stryer, L. (1995) *Biochemistry* (4th Ed.) Freeman, New York, Gait, "Oligonucleotide Synthesis: A Practical Approach" 1984, IRL Press, London, Nelson and Cox (2000), *Lehninger, Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. No. 09/536,841, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. Nos. 60/319,253, 10/013,598, and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (e.g., Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Ser. Nos. 09/916,135, 09/920,491, 09/910,292, and 10/013,598.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983).

Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201, 639; 6,218,803; and 6,225,625, in U.S. Ser. No. 60/364,731 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170.

Additionally, the present invention may have preferred embodiments that include methods for providing genetic information over networks such as the Internet as shown in U.S. Ser. Nos. 10/063,559 (United States Publication No. US20020183936), 60/349,546, 60/376,003, 60/394,574 and 60/403,381.

An array is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, membranes or other solid supports.

Biopolymer or biological polymer: is intended to mean repeating units of biological or chemical moieties. Representative biopolymers include, but are not limited to, nucleic acids, oligonucleotides, amino acids, proteins, peptides, hormones, oligosaccharides, lipids, glycolipids, lipopolysaccharides, phospholipids, synthetic analogues of the foregoing, including, but not limited to, inverted nucleotides, peptide nucleic acids, Meta-DNA, and combinations of the above. Biopolymer synthesis is intended to encompass the synthetic production, both organic and inorganic, of a biopolymer.

Complementary or substantially complementary refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementary exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

A combinatorial synthesis strategy is an ordered strategy for parallel synthesis of diverse polymer sequences by sequential addition of reagents which may be represented by a reactant matrix and a switch matrix, the product of which is a product matrix. A reactant matrix is a 1 column by m row matrix of the building blocks to be added. The switch matrix is all or a subset of the binary numbers, preferably ordered, between 1 and m arranged in columns. A "binary strategy" is one in which at least two successive steps illuminate a portion, often half, of a region of interest on the substrate. In a binary synthesis strategy, all possible compounds which can be formed from an ordered set of reactants are formed. In most preferred embodiments, binary synthesis refers to a synthesis strategy which also factors a previous addition step. For example, a strategy in which a switch matrix for a masking strategy halves regions that were previously illuminated, illuminating about half of the previously illuminated region and protecting the remaining half (while also protecting about half of previously protected regions and illuminating about half of previously protected regions). It will be recognized that binary rounds may be interspersed with non-binary rounds and that only a portion of a substrate may be subjected to a binary scheme. A combinatorial "masking" strategy is a synthesis which uses light or other spatially selective deprotecting or activating agents to remove protecting groups from materials for addition of other materials such as amino acids.

Genome is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

Hybridization refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization."

Hybridization conditions will typically include salt concentrations of less than about 1M, more usually less than about 500 mM and preferably less than about 200 mM. Hybridization temperatures can be as low as 5.degree. C., but are typically greater than 22.degree. C., more typically greater than about 30.degree. C., and preferably in excess of about 37.degree. C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Probes are oligonucleotides capable of binding in a base-specific manner to a complementary strand of nucleic acid. Such probes include peptide nucleic acids, as described in Nielsen et al., *Science* 254, 1497–1500 (1991), and other nucleic acid analogs and nucleic acid mimetics. See U.S. Pat. No. 6,156,501.

Isolated nucleic acid is an object species invention that is the predominant species present (i.e., on a molar basis it is more abundant than any other individual species in the composition). Preferably, an isolated nucleic acid comprises at least about 50, 80 or 90% (on a molar basis) of all macromolecular species present. Most preferably, the object species is purified to essential homogeneity (contaminant species cannot be detected in the composition by conventional detection methods).

Mixed population or complex population refers to any sample containing both desired and undesired nucleic acids. As a non-limiting example, a complex population of nucleic acids may be total genomic DNA, total genomic RNA or a combination thereof. Moreover, a complex population of nucleic acids may have been enriched for a given population but include other undesirable populations. For example, a complex population of nucleic acids may be a sample which has been enriched for desired messenger RNA (mRNA) sequences but still includes some undesired ribosomal RNA sequences (rRNA).

RNA as used herein, includes, polyadenylated and unpolyadenylated RNA, cRNA, pre-mRNA, mRNA, snRNA, snoRNA, siRNA, coding and non-coding RNAs. Pre-mRNA includes partially processed and unprocessed transcripts that may include intronic sequences. Alternative forms of mRNAs also may include intron and exon sequences and 5' and 3' sequences that are not present in all mature forms of the mRNA. Frequently these alternative forms result from alternative splicing. Splicing factors may bind, for example to exon or intron sequences in pre-mRNA. Genes that are alternatively spliced may result in many different mRNA isoforms, some of which may contain intron sequences, 5'UTR sequences or 3' UTR sequences that are not present in other mRNA isoforms from the same gene. Transcript processing may include, for example, splicing, capping, cleavage and polyadenylation and may occur co-transcriptionally or post-transcriptionally. As used herein, a nucleic acid derived from an RNA refers to a nucleic acid for whose synthesis the RNA or a subsequence thereof has ultimately served as a template. Thus, a cDNA reverse transcribed from an RNA, an RNA transcribed from that cDNA, a DNA amplified from the cDNA, an RNA transcribed from the amplified DNA, etc., are all derived from the RNA and detection of such derived products is indicative of the presence and/or abundance of the original transcript in a sample. Thus, RNA derived samples include, but are not limited to, RNA transcripts of the gene or genes, cDNA reverse transcribed from the RNA, cRNA transcribed from the cDNA, DNA amplified from the cDNA, RNA transcribed from amplified DNA, and the like.

Nucleic acids according to the present invention may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793–800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An "oligonucleotide" or "polynucleotide" is a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

A probe is a surface-immobilized molecule that can be recognized by a particular target. Examples of probes that can be investigated by this invention include, but are not restricted to, agonists and antagonists for cell membrane receptors, toxins and venoms, viral epitopes, hormones (e.g., opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

"Solid support", "support", and "substrate" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

A target is a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

Splicing factors are proteins or protein complexes that function in splicing or splicing regulation. Splicing factors include those that are required for constitutive splicing, regulated splicing and splicing of specific messages or groups of messages. A group of related proteins, the SR proteins, see, Zahler et al. *Genes Dev.* 6:837–847 (1992), are required for constitutive pre-mRNA splicing and may also regulate alternative splice-site selection in a concentration-dependent manner. SR proteins have a modular structure that consists of one or two RNA-recognition motifs (RRMs) and a C-terminal rich in arginine and serine residues (RS domain). Their activity in alternative splicing may be antagonized by members of the hnRNP A/B family of proteins. Splicing factors also include proteins that are associated with one or more snRNAs. SR proteins in human include SC35, SRp55, SRp40, SRm300, SFRS10, TASR-1, TASR-2, SF2/ASF, 9G8, SRp75, SRp30c, SRp20 and P54/SFRS11. Proteins in human that are thought to be involved in splice site selection include U2AF65, U2AF35, Urp/U2AF1-RS2, SF1/BBP, CBP80, CBP 20 and PTB/hnRNP I.

The hnRNP proteins in humans include A1, A2/B1, L, M, K, U, F, H, G, R, I and C1/C2. Splicing factors may be stably or transiently associated with a snRNP or with a transcript.

Nascent RNA transcripts from protein-coding genes and mRNA processing intermediates, collectively referred to as pre-mRNA, are generally bound by proteins in the nuclei of eukaryotic cells. From the time nascent transcripts first emerge from RNA polymerase II until mature mRNAs are transported into the cytoplasm, the RNA molecules are associated with an abundant set of nuclear proteins. These proteins are the major protein components of heterogeneous ribonucleoprotein particles (hnRNPs), which contain heterogeneous nuclear RNA (hnRNA), a collective term referring to pre-mRNA and other nuclear RNAs of various sizes.

Splicing is mediated by signals in the sequence of the transcript. These signals include consensus splice sites at the junction between the 5' end of the intron and the 5' exon and the 3' end of the intron and the 3' exon, a branch point region, and polypyrimidine tracts. Polyadenylation is also mediated by signals in the transcript.

Identification of Binding Targets for Regulatory RNA Splicing Factors

In one aspect the present invention provides methods of identifying target RNAs that are bound by specific splicing factors. A nucleic acid sample containing pre-mRNA is incubated with the splicing factor and with an array of probes. A complex is allowed to form, between the pre-mRNA, the splicing factor and a probe that is complementary to the pre-mRNA. The probe may be attached to a solid support at a known or determinable location and the splicing factor may be labeled with a detectable label so that the association of the labeled splicing factor with the probe of known sequence can be detected and the pre-mRNA identified. In one aspect the analysis provides genome-wide analysis of targets that bind the splicing factor. An array of probes that includes a plurality of probes to a selected genome may be used to detect the pre-mRNA-splicing factor complexes. The array may be, for example, a whole genome array or a tiling array. In preferred embodiments the methods are used to identify a plurality of pre-mRNAs that bind the same selected trans-acting splicing factor. In another aspect the array may be an array of beads. The beads may have oligonucleotide probes attached and the probes may comprise a target specific sequence and a tag sequence. By determining the sequence of the tag associated with the bead the sequence of the target specific sequence may be determined. In another aspect the beads may be in solution and each bead may be marked with a detectable label, for example, a colorimetric label.

Splicing of exons proceeds via two sequential transesterification reactions. In each reaction, one phosphate-ester bond is exchanged for another. The net result of these two transesterification reactions is that two exons are ligated and the intervening intron is removed. Introns are removed as a lariat structure in which the 5' G of the intron is joined in an unusual 2',5'-phosphodiester bond to an adenosine near the 3' end of the intron. This A residue is called the branch point. Small nuclear RNAs (snRNAs) and their associated proteins assist in the splicing reaction. Five U-rich snRNAs (U1, U2, U4, U5, and U6), ranging in length from 107 to 210 nucleotides in humans, participate in RNA splicing.

In the nucleus of eukaryotic cells, snRNAs are associated with six to ten proteins in small nuclear ribonucleoprotein particles (snRNPs). Some of these proteins are common to all snRNPs, and some are specific for individual snRNPs. Experiments with a synthetic oligonucleotide that hybridizes with the 5'-end region of U1 snRNA and later studies with pre-mRNAs that were mutated in the 5' splice-site consensus sequence provided strong evidence that base pairing between the 5' splice site of a pre-mRNA and the 5' region of U1 snRNA is required for RNA splicing.

Involvement of U2 snRNA in splicing initially was suspected when it was found to have an internal sequence that is largely complementary to the consensus sequence flanking the branch point in pre-mRNAs. Mutation experiments, similar to those conducted with U1 snRNA and 5' splice sites, demonstrated that base pairing between U2 snRNA and the branch-point sequence in pre-mRNA is critical to splicing. These studies with U1 and U2 snRNAs indicate that during splicing they base-pair with pre-mRNA.

In higher eukaryotes there is also a minority class of introns that are excised by a distinct low-abundance spliceosome that includes the U12 snRNP instead of the U2 snRNA. In addition, in the U12 dependent spliceosome U1, U4 and U6 snRNPs are replaced by the U11, U4atac and U6atac snRNPs. Both the U2 and U12 spliceosomes share the U5 snRNP (see, McConnell et al. RNA (2002) 8:579–586, Tarn and Steitz, TIBS 22:132–7 (1997) and Burge et al. 1999). The U2 dependent spliceosome excises U2 dependent introns while the U12 dependent spliceosome excises U12 dependent introns. Whether an intron is U2 or U12 dependent is determined by sequences present in the intron. U2 dependent introns have loosely conserved sequences at the branchpoint as well as at the 5' and 3' splice site, the most conserved features being terminal dinucleotides GT and AG. U12-dependent introns contain more highly conserved sequences at the 5' splice site and branch-point. A search of the sequence of the human genome identified over 400 candidate U12-type introns (Levine and Durbin, 2001) although fewer than 10 introns have been demonstrated to splice in a U12-dependent manner.

Similar studies with other snRNAs demonstrated that RNA-RNA interactions involving them also occur during splicing. For example, an internal region of U6 snRNA initially base-pairs with the 5' end of U4 snRNA. Rearrangements later in the splicing process result in U6 snRNA base pairing with the 5' end of U2 snRNA, which remains base-paired to the branch-point sequence in the intron. Later in the splicing process, base pairing of U5 snRNA with four exon nucleotides adjacent to the splice sites displaces U1 snRNA from the pre-mRNA.

Based on the results of these experiments, identification of reaction intermediates, and other biochemical analyses, the five splicing snRNPs are thought to sequentially assemble on the pre-mRNA forming a large ribonucleoprotein complex called a spliceosome. Assembly of a spliceosome begins with the base pairing of U1 and U2 snRNAs, as part of the U1 and U2 snRNPs, to the pre-mRNA. Extensive base pairing between the snRNAs in the U4 and U6 snRNPs forms a complex that associates with U5 snRNP. The U4/U6/U5 complex then associates, presumably via protein-protein interactions, with the previously formed complex consisting of a pre-mRNA base-paired to U1 and U2 snRNPs to yield a spliceosome.

After formation of the spliceosome, extensive rearrangements occur in the pairing of snRNAs and the pre-mRNA, as noted previously. The rearranged spliceosome then catalyzes the two transesterification reactions that result in RNA splicing. After the second transesterification reaction, the ligated exons are released from the spliceosome while the lariat intron remains associated with the snRNPs. This final intron-snRNP complex is unstable and dissociates. The individual snRNPs released participate in a new cycle of splicing.

It is estimated that at least one hundred proteins are involved in RNA splicing. Some of these splicing factors are associated with snRNPs, but others are not. Sequencing of yeast genes encoding splicing factors has revealed that they contain domains with the RNP motif, which interacts with RNA, and the SR motif, which interacts with other proteins and may contribute to RNA binding. Some splicing factors also exhibit sequence homologies to known RNA helicases; these may be necessary for the base-pairing rearrangements that occur in snRNAs during the spliceosomal splicing cycle.

The recent completion of the sequencing of the human genome resulted in a revision of the number of human genes down from a high estimate of about 150,000 to the unexpectedly low current estimate of about 32,000, see, International Human Genome Sequencing Consortium, *Nature* 409: 860–921 (2001) and Venter et al., *Science* 291:1304–1351 (2001). This suggests that the number of different types of mRNAs is much higher than the number of genes, indicating that alternative splicing may account for much additional complexity. The increased importance of alternative splicing has resulted in an increased interest in understanding the mechanisms and regulation of splicing. In particular, methods that facilitate genomic analysis of alternative splicing, including identification of alternative splice forms, determination of the functional roles of alternatively spliced forms and determination of modes of regulation of alternative splicing will become increasingly useful.

Recent studies estimate that 35–59% of human genes show evidence of at least one alternative splice form, see, for example, Modrek and Lee, *Nat. Genet.* 30:13–19 (2002), Mironov et al., *Genome Res* 9:1288–1293 (1999), and Modrek et al., *Nucleic Acid Res.* 29:2850–2859 (2001). Relatively little is known about the mechanisms of how alternative splicing is regulated. Alternative splicing results in different mRNAs being generated from the same transcribed sequence. In this way a single gene may generate a dozen or more different mRNAs. Variation in mRNA structure may result, for example, from exons that are present in some mRNAs but spliced out of others (exon skipping), introns that are normally excised can be retained in the mRNA (intron retention), the position of the 5' or 3' splice site can be shifted to make exons longer or shorter (alternative splice donor or acceptor site use), and the site of polyadenylation can vary. The start site of transcription can also vary, resulting in differences in the 5' UTR. These changes may be regulated, for example, depending on sexual genotype, cellular differentiation or that activation of cell signaling pathways.

Alternative splicing is mediated by the binding of trans-acting protein factors to cis-acting sequences within the pre-mRNA leading to differential use of splice sites. Many cis-acting sequences have been identified and they may be grouped as either enhancer or suppressor elements (for a review on splicing regulatory elements, see Ladd and Cooper, *Genome Biol.* 3(11):reviews0008.1–0008.16. (2002). In general, the auxiliary elements that regulate the usage of alternative splice sites are small (for example, 8–10 nucleotides long), variable in sequence, individually weak, thought to be poorly conserved and present in multiple copies. They are usually single-stranded, although secondary structure has been implicated in the function of a few elements. Auxiliary elements are difficult to identify because they contain degenerate sequence motifs. They can be exonic or intronic. Intronic elements may be close to the exon they regulate but they can be upstream, downstream, or flanking both sides of the regulated exon. Intronic elements can also be proximal (within 100 nucleotides) or distal (more than one kilobase away from the regulated exon) or between 100 and 1000 bases from the regulated exon. Auxiliary elements can enhance or repress splice-site selection and can compete with other auxiliary elements and the factors that bind them.

Splicing factors recognize the auxiliary elements and direct the splicing machinery to splice the RNA and specific splicing factors that regulate the splicing of specific genes or groups of genes will interact directly with the transcripts from those genes. A number of regulated splicing events that are controlled by trans-acting factors have been demonstrated. Alternative splicing of exon 5 of the cardiac troponin T transcript is regulated by binding of members of the CUG-binding protein (CUG-BP), embryonically lethal abnormal vision-type RNA binding protein 3 (ETR-3)-like factor (CELF) family and pyrimidine tract-binding protein (PTB). The neuron-specific N1 exon of the c-src proto-oncogene is also regulated by PTB as well as KH-type splicing-regulatory protein (KSRP), far upstream element binding protein (FBP), and the heterogeneous nuclear ribonucleoproteins hnRNP H and hnRNP F. PTB also regulates neuron-specific splicing of several other targets, and may be antagonized by binding to the RNA of the neuron-specific activator neurooncological ventral antigen 1 (Nova-1). Other splicing factors include the two subunits of U2 auxiliary factor (U2AF) and alternative splicing factor/splicing factor 2 (ASF/SF2). See also, Hovhannisyan and Carstens, *Mol. Cell Biol.* 25:250–263 (2005), Zhu et al., *Oncogene* 23:7545–51 (2004), and Black, *Annual Rev. Biochem.* 72:291–336 (2003).

Figure 1:
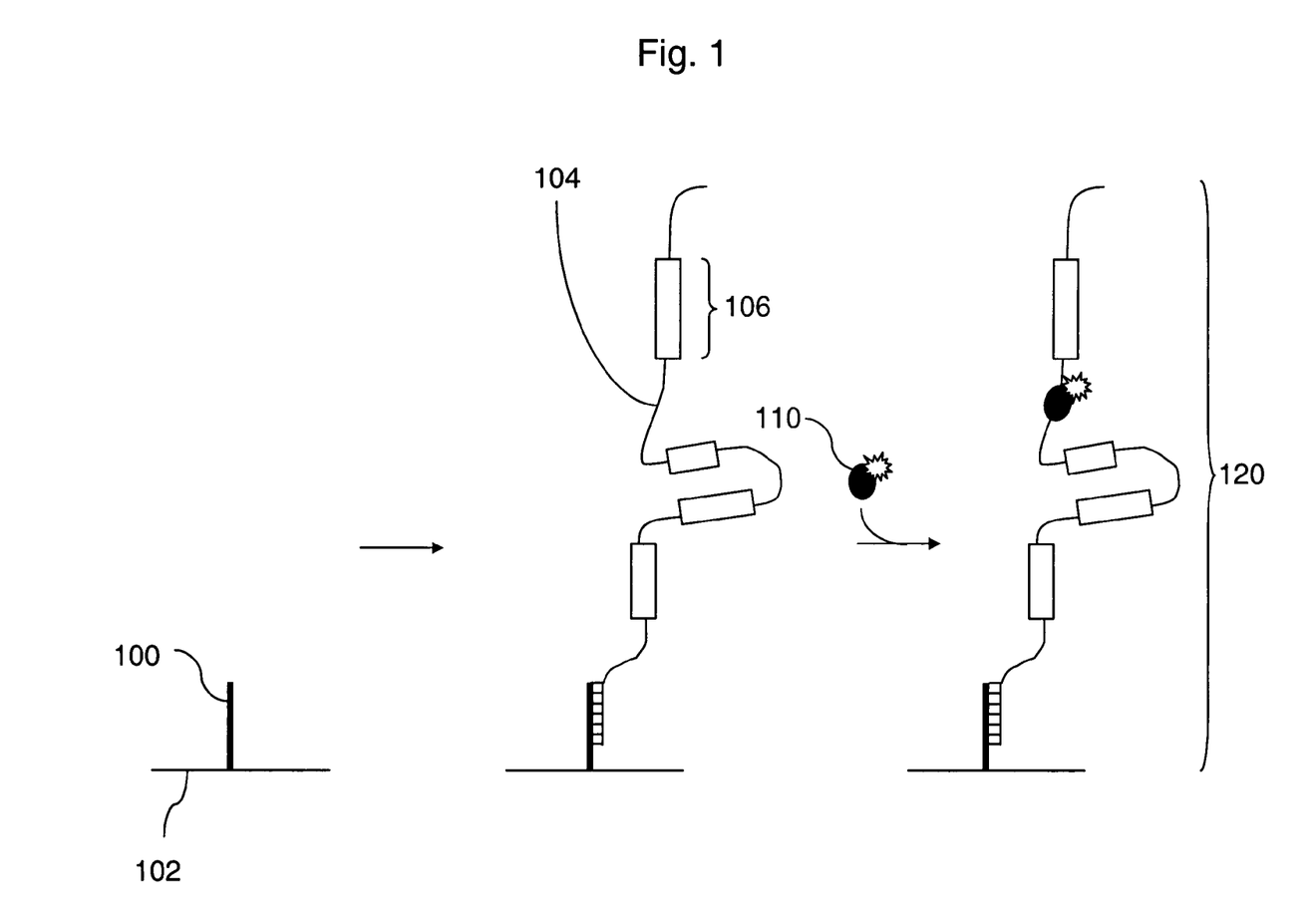
FIG. 1 shows a schematic of a method to capture unprocessed RNA on a solid support and then use the captured unprocessed RNA to capture splicing factors. The transcripts that are bound by a selected splicing factor may be identified.

Methods to identify genes whose splicing may be regulated by specific splicing factors are disclosed. FIG. 1 shows a schematic of one aspect of the method. A probe (100) bound to a solid support (102) is contacted with an RNA (104) that contains sequences that are not present in the mature mRNA. The RNA (104) is captured on the solid support (102) by hybridization to the probe (100), resulting in array bound pre-mRNA. The exons (106) are represented by boxes and the introns and 5' and 3' UTR are represented by lines. The captured RNA is contacted with a labeled splicing factor (110). Interaction of the splicing factor (110) with the captured RNA (104) results in a complex (120) including the probe, the RNA and the splicing factor, resulting in association of label with the probe. The probe is present at a known or determinable location and has a known or determinable sequence so the sequence of the captured RNA can be determined. The splicing factor may be multiple proteins and may include one or more RNAs and unlabeled proteins or splicing factors may also be part of the complex. For example, some splicing factors may require prior binding of another factor to the pre-mRNA before they will bind and in some embodiments these auxiliary factors are also contacted with the array bound RNA.

One or more target transcripts that associate with or bind to a selected splicing factor or RNA binding protein may be identified. Groups of transcripts that are bound by the same RNA binding protein or splicing factor or factors may be regulated in a coordinated manner or in the same manner. In one aspect a plurality of transcripts that specifically bind the same splicing factor or factors are identified. The genes that generate the transcripts may also be identified. Binding of the factor may be specific to the gene or to a particular isoform of RNA transcribed from the gene. The unprocessed RNA transcripts may be labeled as a result of association with or binding to the splicing factor or factors of interest and the identity of the labeled transcripts is determined by sequence specific hybridization to an array of probes or to a probe attached to a bead. The array comprises probes that are complementary to transcripts and are present on the array at known or determinable locations.

Regulation of alternative splicing is complex and not well understood, but the choice of splice sites is thought to be directed by proteins that bind to non-splice site RNA elements and enhance or repress spliceosome assembly nearby. Splicing regulators included members of the SR family of proteins as well as factors generally classed as hnRNP proteins. SR proteins can bind to elements within exons to stimulate spliceosome assembly. Along a given pre-mRNA multiple different SR and hnRNP proteins may bind to specific sequence elements.

Regulation of gene expression may be modulated by regulation of post transcription processing events. Splicing of a transcript may be regulated, for example, in a tissue specific, temporal, or developmental manner or in response to environmental cues. Splicing may be regulated by cis acting regulatory elements, such as exonic splicing enhancers and by trans acting protein factors, such as SR proteins and proteins that regulate specific genes or groups of genes. As is observed in transcriptional regulation it is likely that groups of transcripts that are coordinately regulated will interact with the same specific regulatory factors. For a review of mechanisms of alternative splicing see, Black, D. L. *Ann Rev Biochem* 72:291–336 (2003).

In some aspects the pre-mRNA bound by one or more splicing factors is co-immunoprecipitated with the splicing factor and identified by hybridization to an array. Methods of identifying genomic regions that bind to a protein of interest using chromatin immunoprecipitation have been described. See, for example, U.S. Pat. No. 6,410,243. In general, this method identifies a region of a genome to which a protein of interest binds by crosslinking the genomic DNA of the cell using formaldehyde, separating the DNA fragments to which the protein of interest is bound, from the mixture by immunoprecipitation using an antibody that binds specifically to the protein of interest, separating the DNA fragment from the protein, amplification and labeling of the DNA fragment and detecting the labeled DNA fragment using a microarray. This method allows for unbiased genome-wide analysis of fragments bound to selected proteins. To identify RNA bound to splicing factors the RNA bound to the factor or factors of interest may be crosslinked to the protein, although crosslinking is not required, and the RNA that is bound is separated from the unbound RNA by immunoprecipitation using an antibody that specifically binds the protein of interest. The RNA may be amplified and labeled and detected using a microarray. For examples of cross linking methods see, Rinke-Appel and Brimacombe, Chpt. 11 in RNA:Protein Interactions, A Practical Approach, ed. C. W. J. Smith (1998).

In one aspect of the present invention methods for identifying transcripts that interact with a selected splicing factor or factors are identified using an array of probes. Groups of transcripts that may be coordinately regulated may be identified based on interaction with a common splicing factor. A plurality of target RNAs that are bound specifically by the splicing factor may be identified.

In one embodiment, shown in FIG. 1, RNA is captured on an array of probes. In some aspects pre-mRNA is preferentially captured by probes on the array that are complementary to sequences that are present in the pre-mRNA but not in the mRNA, for example, intronic sequences. In some embodiments probes to both exonic and intronic sequence are included on the array as well as probes to the 5' and 3' UTRs. Probes may be designed to specifically detect alternative RNA isoforms resulting from alternative splicing, use of alternate polyadenylation sites or alternate transcription start sites. In some embodiments the array may include probes to inton-exon junctions and to exon-exon junctions and these junction probes may be designed to detect specific alternatively spliced forms of an mRNA.

The array may also comprise probes that are complementary to regions that are present in both pre-mRNA and mRNA. Nucleic acids that are not complementary to a probe on the array may be removed by washing. The array with bound pre-mRNA may then be incubated with a specific regulatory splicing factor. In a preferred embodiment the splicing factor is labeled with a detectable label. Hybridization of the splicing factor to a feature or features of the array is detected and the probes that have splicing factor associated are identified to determine which genes may be regulated by that splicing factor. The splicing factor may be a single protein, a complex of one or more proteins, a fragment of a protein or a ribonucleoprotein particle.

A nucleic acid sample that includes pre-mRNA may be obtained by any method known in the art. In some aspects total RNA comprising unprocessed and partially processed RNA is obtained from a sample. The sample may be enriched for unprocessed and partially processed RNAs. Transcripts that are not fully processed may be present in a cell for a variety of reasons, for example, the transcript may have been in the process of being spliced when the cells were disrupted, there may be a mutation present in the transcript that blocks or inhibits splicing, there may be a mutation in the cell that blocks or inhibits the processing of one or more transcripts, or the cells may be exposed to an environmental condition that blocks or inhibits splicing, for example, a yeast strain carrying a temperature sensitive splicing mutation may be shifted to the non-permissive temperature for a period of time before RNA is isolated.

Methods for labeling proteins with detectable labels are well known in the art. Proteins may be labeled, for example, with radioactivity, fluorescent dyes and biotin. Dyes may be amine reactive and include, for example, fluorescein, fluroescein-EX, FITC, Oregon Green, tetramethylrhodamine, rhodamine Red-X, and Texas Red-X. Biotin and Biotin/DNP may also be used. In another embodiment, after the splicing factor is bound the array is incubated with an antibody that binds to the splicing factor and bound antibody is detected. In some aspects that protein may be bound to the pre-mRNA before contacting with the array of probes. The pre-mRNA and splicing factor may be crosslinked to enhance the stability of the complex.

In one aspect the nucleic acid sample comprising pre-mRNA is hybridized to an array that includes more than 10,000, more than 100,000 or more than 1,000,000 different sequence probes. Probes that have the same sequence are present in the same feature or features of the array at known or determinable locations so the RNAs that are bound may be identified by identifying the probe feature that the RNA is bound to. In many aspects the array will include a plurality of different sequence probes that are complementary to each RNA to be detected. In one embodiment the array is designed with probes to transcripts that may be alternatively spliced. The probes of the array may be complementary to intronic regions of the transcripts so that unspliced transcripts will bind to the array. Unprocessed transcripts or pre-mRNA contain sequence that is not present in the final processed RNA or are present in only some forms of the mRNA. Probes designed to hybridize to those sequences will detect the unprocessed RNA but not the processed RNA. An array of probes may be designed with probes and probe sets that are designed to hybridize to regions of transcripts that will be removed from the processed RNA. These probe sets should specifically detect unprocessed RNA.

Splicing factors may be isolated by any method known in the art, for example, they may be purified from an endogenous source or be produced recombinantly. The proteins may be, for example, tagged and purified with a resin that has affinity for the tag, for example a 6-histidine tag purified using a resin with immobilized nickel ions (see, for example, the QIAexpress Ni-NTA Protein Purification System, available from Qiagen) or glutathione-S-transferase (GST). The proteins may be labeled during synthesis or after synthesis. In another embodiment antibodies to the protein or proteins of interest may be used to detect the complex between a transcript and a splicing factor. If the splicing factor is a fusion protein tagged with a tag such as GST or 6-HIS, an antibody that recognizes the tag may be used to detect the complex. Proteins may be essentially pure or part of a fraction that includes a mixture of proteins, for example, a splicing extract or fraction thereof. A specific RNA binding protein may be isolated by affinity chromatography using, for example, affinity to a specific sequence of RNA, see for example, Kaminski et al. p137–160 in RNA: Protein Interactions, Ed. Smith (1998). A splicing factor may be a complex of proteins, for example a snRNP. A splicing factor may be obtained from a first organism and may be contacted with array captured pre-mRNA from a second organism. For example, human pre-mRNA may be captured on an array and contacted with a splicing factor from mouse. In some embodiments the array captured pre-mRNA is contacted with a purified snRNP or a fraction containing a purified snRNP. The snRNP may be an intron specific snRNP, one that associates with only a subset of introns, like the U12 snRNP, and the method may be used to identify genes that are regulated by the intron specific snRNP.

In another aspect a polypeptide that is a fragment of a splicing factor may be used to contact the array bound RNA. For example, a fragment of the splicing factor including the RNA binding domain may be used to label target RNAs. The fragment may be, for example, a single domain of the splicing factor or a plurality of domains. The labeled splicing factor or fragment thereof may be mixed with the array bound RNA in the presence of one or more unlabeled proteins or factors that may facilitate or be required for specific binding of the factor to its target RNAs.

In other aspects methods are disclosed for identifying target RNAs for RNA binding proteins that are involved in other processes, for example, capping, polyadenylation, transport and translation. In general RNAs are captured on an array and the array-bound RNAs are contacted with the suspected RNA binding protein, the complexes that include the RNA binding protein are labeled and detected to identify the transcripts that are bound by the RNA binding protein.

The nucleic acid sample can be an amplification product of a nucleic acid sample obtained from a biological source. For example, total RNA may be isolated from a biological sample and amplified by a method such as the method described in U.S. Pat. Nos. 5,545,522 and 5,891,636, or the methods described in U.S. Pat. No. 6,794,138 and U.S. Patent Publication Nos. 20040214210, 20040132056 and 20020120409. If amplification products are to be used the RNA that is captured is preferably the same orientation as the starting RNA so that signals in the RNA required for recognition of the RNA are present.

The nucleic acid sample may be fragmented so that only a portion of the target is bound by the splicing factor. Because many of the cis-acting sequence elements are small the splicing factor may be able to recognize fragments of the pre-mRNA. The RNA in the sample may also be amplified. For example, RNA may be amplified by reverse transcription followed by in vitro transcription of copies of the RNA, but the RNA that is hybridized to the splicing factor should be in the same orientation as the transcribed RNA (sense orientation) to preserve the cis-acting sequence elements.

In some aspects more than one splicing factor is allowed to form complexes with the pre-mRNA. Some splicing factors may bind only after another splicing factor, such as a constitutive splicing factor, has bound. In one aspect only one of the splicing factors is labeled and the other one or more splicing factors are not labeled.

For additional information on methods that may be used for analysis of RNA:Protein interactions see, RNA:PROTEIN INTERACTIONS; A PRACTICAL APPROACH, Ed. C. W. J. Smith (1998) Oxford University Press, New York, N.Y. See also, Protein Structure: A Practical Approach, Ed. T. E. Creighton ($2^{nd}$ ed), (1997) Oxford University Press, New York, N.Y. and Protein Function: A Practical Approach, Ed. T. E. Creighton ($2^{nd}$ ed), (1997) Oxford University Press, New York, N.Y.

CONCLUSION

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled.

I claim:

1. A method of identifying one or more RNA transcripts that are bound by a splicing factor comprising:
   obtaining a nucleic acid sample comprising pre-mRNA;
   contacting the nucleic acid sample with an array of nucleic acid probes to generate array-bound pre-mRNA, wherein the array comprises probes that are complementary to a plurality of introns;
   contacting the array-bound pre-mRNA with a splicing factor to allow formation of complexes comprising the splicing factor and array-bound pre-mRNA; and
   identifying one or more probes of the array that are in a complex comprising the splicing factor to identify one or more pre-mRNA that is bound by the splicing factor.

2. The method of claim 1 wherein the nucleic acid sample is obtained by isolating nucleic acid that is bound to heterogenous nuclear ribonucleoprotein particles.

3. The method of claim 2 wherein the heterogenous nuclear ribonucleoprotein particles are isolated by immunoprecipitation.

4. The method of claim 1 wherein the splicing factor is labeled with a first detectable label.

5. The method of claim 1 wherein the array bound RNA is contacted with a second splicing factor.

6. The method of claim 5 wherein the second splicing factor is labeled with a second detectable label that may be different from the first detectable label.

7. The method of claim 5 wherein the second splicing factor is unlabeled.

8. The method of claim 1 wherein the splicing factor is an SR protein.

9. The method of claim 1 wherein the splicing factor is an hnRNP protein.

10. The method of claim 1 wherein the splicing factor is selected from the group consisting of CUG-BP, a member of the CELF family, PTB, KSRP, FBP, hnRNP H, hnRNP F, hnRNP K, hnRNP A1 and Nova-1.

11. The method of claim 1 wherein the step of identifying the probe or probes of the array that are bound to one or more of the complexes is by detecting the association of an antibody with one or more of the complexes.

12. The method of claim 11 wherein the antibody binds to the splicing factor.

13. The method of claim 11 wherein the splicing factor is tagged and the antibody binds to the tag.

14. A method of identifying a plurality of transcripts that bind a selected splicing factor comprising:
   obtaining a nucleic acid sample comprising unprocessed or partially processed RNA transcripts;
   hybridizing the nucleic acid sample to an array of capture probes that are complementary to pre-mRNA and capturing pre-mRNA on the array;
   contacting the array and captured pre-mRNA with a splicing factor and detecting the probes of the array that are in a complex with the splicing factor; and,
   identifying pre-mRNA that is in a complex with the splicing factor by determining the sequence of the probes of the array that are in complex with the splicing factor.

15. The method of claim 14 wherein the splicing factor is labeled with a detectable label.

16. The method of claim 15 wherein the step of detecting the probes of the array that are in a complex with the splicing factor is by detecting the probes of the array that are associated with the detectable label.

17. The method of claim 14 wherein the step of detecting probes of the array that are in a complex with the splicing factor is by mixing an antibody that specifically binds to the splicing factor with the array and detecting the presence of bound antibody.

18. The method of claim 14 wherein the splicing factor comprises a plurality of polypeptides.

19. The method of claim 14 wherein the splicing factor comprises a ribonucleoprotein particle.

20. The method of claim 14 wherein the splicing factor is selected from the group consisting of and SR protein and an hnRNP protein.

* * * * *